United States Patent [19]

Zanzi

[11] Patent Number: Plant 6,897

[45] Date of Patent: Jul. 4, 1989

[54] PEAR TREE — RED WINTER

[75] Inventor: Giovanni Zanzi, Ferrara, Italy

[73] Assignee: Zanzivivai-Ferrara S.r.l., Fossanova San Marco, Italy

[21] Appl. No.: 145,498

[22] Filed: Jan. 15, 1988

[51] Int. Cl.[4] ..... A01H 5/00

[52] U.S. Cl. ..... Plt./36

[58] Field of Search ..... Plt./36

*Primary Examiner*—Robert E. Bagwill

*Attorney, Agent, or Firm*—Bryan & Levitin

[57] ABSTRACT

A new and distinct asexually reproduced pear tree called Red Winter, as illustrated and described. The fruit is large, light yellow-red in color and has a very sweet flavor. It ripens approximately thirty-five days after the William Bartlett variety and has an exceptionally long shelf life under the conditions existing in the Ferrara region of Northern Italy.

1 Drawing Sheet

DESCRIPTION OF THE INVENTION

The present invention relates to a novel asexually reproduced pear tree which has been named Red Winter and which produces a beautiful fruit with an unusually long shelf-life. The fruit from the new tree is similar in shape to a prized pear variety known as "Decana del Comizio," but the Red Winter fruit is larger and more colorful. This new pear is valued for its large size, averaging 200 grams (3.2 ounces), its light yellow-red color and white flesh and its very sweet and pleasing flavor.

The Red Winter pear tree was developed and propagated, beginning in 1981, by its inventor through grafting of buds obtained from a branch of a pear tree of an old variety called "Pera dell 'Azzuna," grown in the village of Arzana near Ostellato (Ferrara) on the farm land called "Olmo", owned by Societe Agraria Padana S.A.P. S.r.l., onto quince trees on the inventor's farm, "Portoncino", in the town of Piumazzo di Modena. Production was commenced in 1984 and has continued to improve steadily through 1987, despite a season of cold spring weather not normally favorable for fruit setting.

The drawing shows a photograph of the new pear variety as well as leaves of the tree.

Characteristics of the new pear variety are:

FRUIT

Size:

*Average weight.*—200 grams, very uniform. Ripe pears have a maximum length of 3.6 inches.

*Shelf life.*—Approximately ten months, that is, from September (date of ripening) through June of the following year.

Shape: Pyriform.

Color: Very bright yellow-red color. The color chart designations for Red Winter pears (Universal Code of Colors — E. Seguy) are: Bottom Color of ripe fruit — No. 318; Overcolor red — No. 168.

Flesh: White, ice-colored, very firm, fine grain, melting when near ripening.

Flavor: Very sweet, excellent tasting.

Storage capacity: Can be kept in normal cold storage until the following summer, without danger to fruit quality.

Flowering: Very abundant and close during middle period.

Preferred pollinators: William, Conference.

Ripening: Early September.

TREE

Vigor: Good.

Wood color: Light brown-green, becoming bright green in those areas with younger vegetation.

Leaf: Light green, turgid, with oval shape and whitish-green peduncle having a normal length.

Pruning: Palmette structure preferred, but can easily support all kinds of pruning.

Productivity: Very high.

What is claimed is:

1. A new and distinct asexually reproduced pear variety, characterized by its large size, bright skin and light yellow-red color and exceptional durability in storage, substantially as illustrated and described.

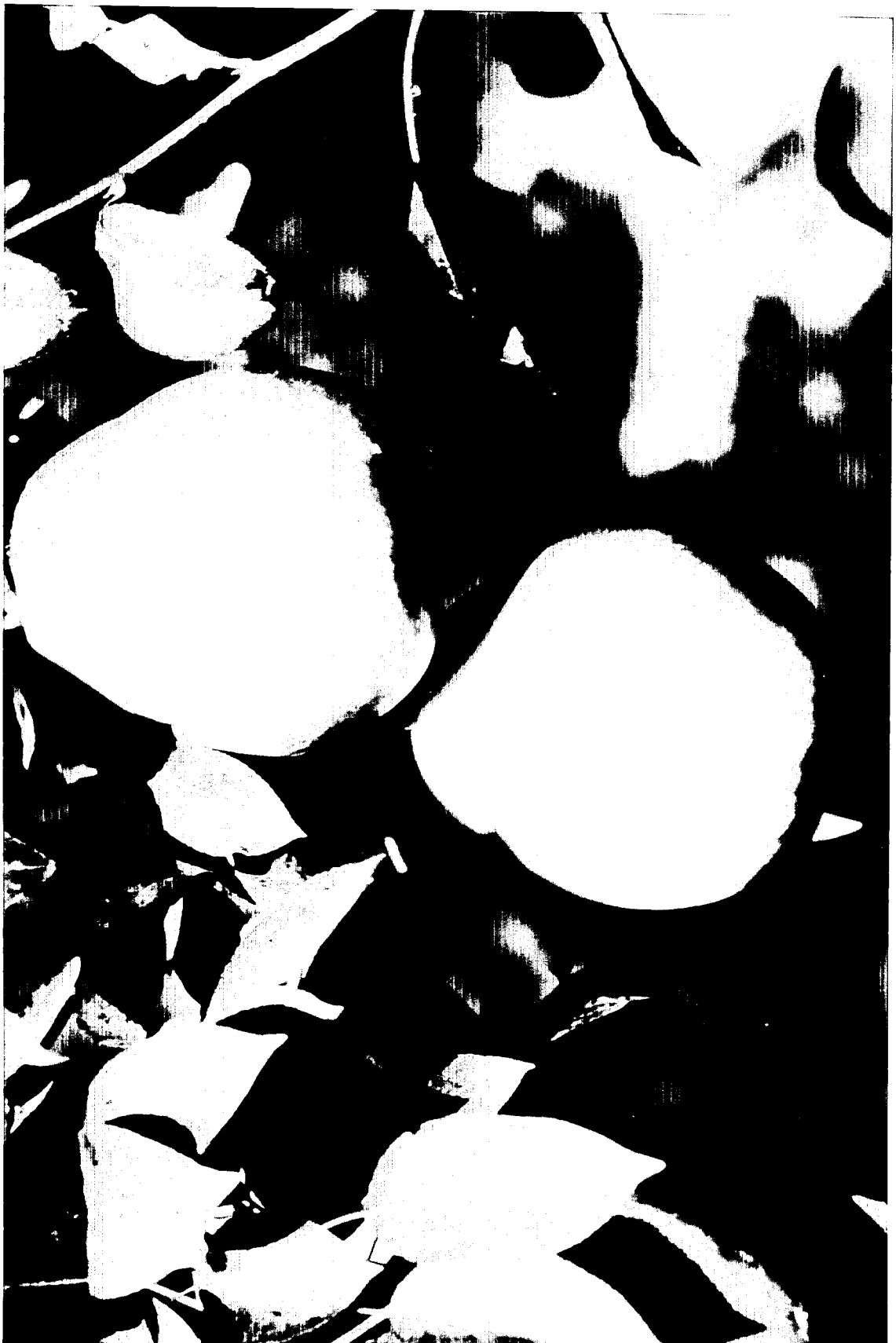

* * * * *